United States Patent [19]
Reed et al.

[11] Patent Number: 5,569,272
[45] Date of Patent: Oct. 29, 1996

[54] TISSUE-CONNECTIVE DEVICES WITH MICROMECHANICAL BARBS

[75] Inventors: Michael L. Reed; Lee E. Weiss, both of Pittsburgh, Pa.

[73] Assignee: Carnegie Mellon University, Pittsburgh, Pa.

[21] Appl. No.: 193,385

[22] Filed: Feb. 8, 1994

Related U.S. Application Data

[63] Continuation of Ser. No. 648,275, Jan. 31, 1991, Pat. No. 5,312,456.
[51] Int. Cl.$^6$ .................................................. A61B 17/00
[52] U.S. Cl. ........................... 606/151; 606/153; 673/12; 604/46
[58] Field of Search ..................... 606/151, 153, 606/154–158, 150, 220, 228; 623/1, 12; 604/46

[56] References Cited

U.S. PATENT DOCUMENTS

| | | | |
|---|---|---|---|
| H356 | 11/1987 | Stokes et al. | 128/785 |
| 1,151,300 | 8/1915 | Soresi | 606/153 |
| 3,221,746 | 12/1965 | Noble | 606/155 |
| 4,008,338 | 2/1977 | Strandine et al. | 604/46 |
| 4,060,089 | 11/1977 | Noiles | 606/220 |
| 4,553,542 | 11/1985 | Schenk et al. | 606/153 |
| 4,665,917 | 5/1987 | Clanton et al. | 606/153 |
| 5,104,399 | 4/1992 | Lazarus | 606/153 |
| 5,207,695 | 5/1993 | Trout, III | 606/153 |
| 5,234,448 | 8/1993 | Wholey et al. | 606/153 |

Primary Examiner—Stephen C. Pellegrino
Assistant Examiner—Jeffrey A. Schmidt
Attorney, Agent, or Firm—Reed Smith Shaw & McClay

[57] ABSTRACT

A system for linking a first member with a second member. The system is comprised of a first plurality of micromechanical barbs disposed on the first member. The system is also comprised of a second plurality of micromechanical barbs disposed on the second member. The barbs on the first member and the second member are of a shape such that a locking connection is formed between the first member and second member through the first plurality and second plurality of barbs when placed together. Each of the barbs of the first plurality and second plurality of barbs extend from the first member and second member, respectively, to a height no greater than 5 millimeters. The present invention also pertains to a micromechanical barb for linking with an object. The micromechanical barb comprises a base. The micromechanical barb is also comprised of a support which extends from the base. The micromechanical barb additionally is comprised of a head which is disposed upon the support and which mates with the object such that a locking connection is found therebetween. The length of the support and the head is less than 5 millimeters.

13 Claims, 11 Drawing Sheets

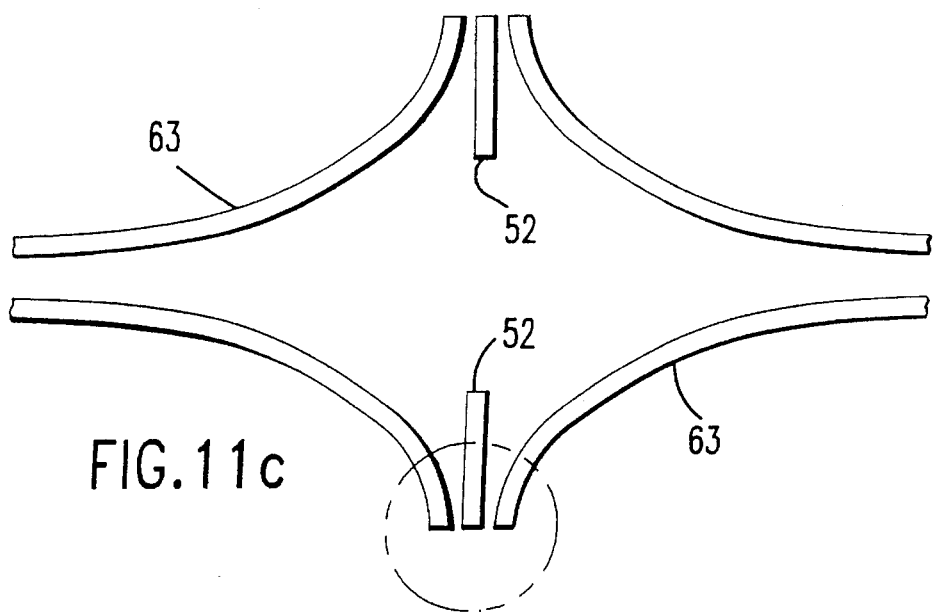
FIG.11c
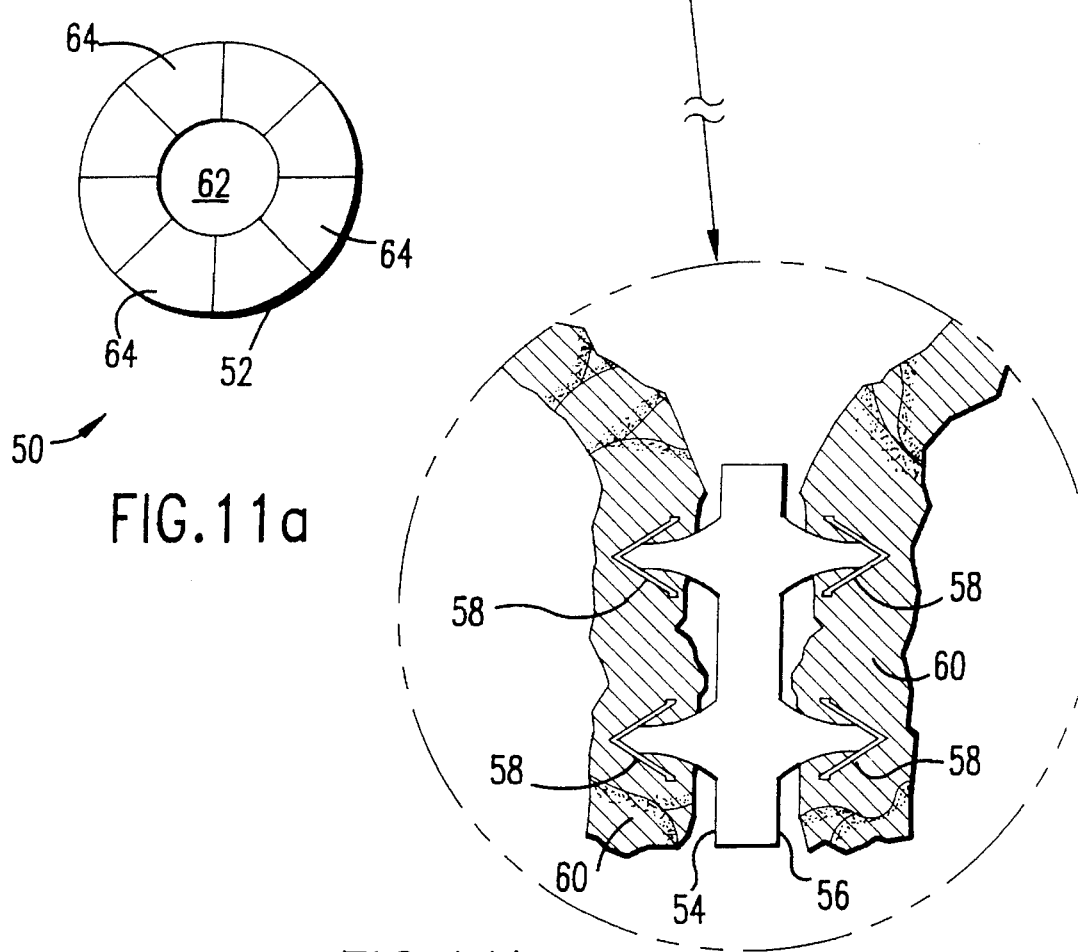
FIG.11a
FIG.11b

TISSUE-CONNECTIVE DEVICES WITH MICROMECHANICAL BARBS

This is a continuation of application Ser. No. 07/648,275 filed on Jan. 31, 1991 now U.S. Pat. No. 5,312,456.

FIELD OF THE INVENTION

The present invention pertains to fastening systems. More specifically, the present invention pertains to a micromechanical barb as well as a system and method for its use.

BACKGROUND OF THE INVENTION

There is essentially an infinite need for linking two distinct members or objects to each other. Some common techniques for linking two distinct objects are adhesively bonding them together with, for instance, glue, soldering them together or fastening them together with, for instance, a nail or nut and bolt arrangement to name but a few of the techniques. However, as the size of the objects to be linked becomes smaller and approaches the microscope level, many of the techniques for linking larger objects are no longer available.

With the advent of technologies that allow for the relatively easy production of microminiature devices and components, the ability to link such devices or components becomes an increasingly important problem. While adhesives are available for use, due to their chemical nature, not all environments are conducive to their use to link microminiature components or objects. What is needed is a more versatile technique to link microminiature objects.

SUMMARY OF THE INVENTION

The present invention pertains to a system for linking a first member with a second member. The system is comprised of a first plurality of micromechanical barbs disposed on the first member. The system is also comprised of a second plurality of micromechanical barbs disposed on the second member. The barbs on the first member and the second member are of a shape such that a locking connection is formed between the first member and second member through the first plurality and second plurality of barbs when placed together. Each of the barbs of the first plurality and second plurality of barbs extend from the first member and second member, respectively, to a height no greater than 5 millimeters. The first plurality of barbs and second plurality of barbs oppose each other.

The present invention also pertains to a micromechanical barb for linking with an object. The micromechanical barb comprises a base. The micromechanical barb is additionally comprised of a support which extends from the base. The micromechanical barb additionally is comprised of a head which is disposed upon the support and which mates with the object such that a locking connection is found therebetween. The length of the support and the head is less than 5 millimeters.

The present invention also pertains to a method for making a plurality of barbs. The method is comprised of the steps of first forming a substrate of a first material with a layer of a second material thereon, and at predetermined discrete locations on the layer a third material. Next, there is the step of removing portions of the layer and the substrate such that a frustrum shape is formed on the surface of the substrate. Next, there is the step of removing the third material but leaving the first and second materials essentially untouched. Then, there is the step of reforming the layer made of the second material on the frustrum surface of the substrate. Next, there is the step of removing portions of the layer at essentially the center of the lowest points of the frustrum. There is then the step of removing portions of the substrate but not the second material such that a plurality of barbs is created.

The present invention additionally pertains to a connector produced by surface micromachining. The connector comprises a first portion which lockingly connects with an object. The connector is also comprised of a base upon which the first portion is fixedly disposed.

BRIEF DESCRIPTION OF THE DRAWINGS

In the accompanying drawings, the preferred embodiments of the invention and preferred methods of practicing the invention are illustrated in which:

FIGS. 11a–c are schematic representations of an apparatus for connecting tissue.

DESCRIPTION OF THE PREFERRED EMBODIMENT

Figure 1:
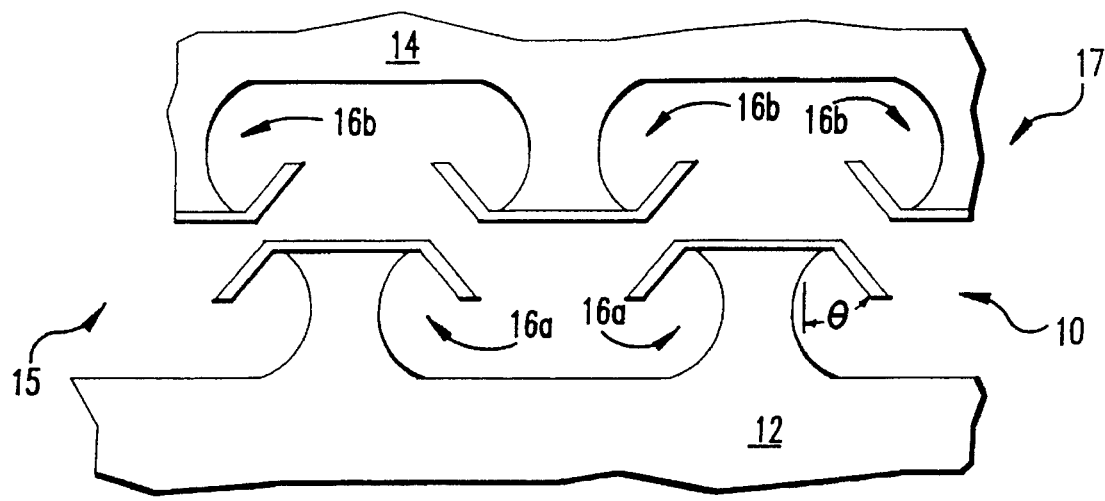
FIG. 1 is a schematic representation of a cross section of a first plurality of barbs and a second plurality of barbs adjacent to each other.

Referring now to the drawings, wherein like reference numerals refer to similar or identical parts throughout the several views, and more specifically to FIG. 1 thereof there is shown a system 10 for linking a first member 12 with a second member 14. The system comprises a first plurality of micromechanical barbs 16a disposed on the first member 12. The system 10 is also comprised of a second plurality of micromechanical barbs 16b disposed on the second member 14. The barbs 16a on the first member 12 and the barbs 16b on the second member 14 are of a shape such that a locking connection is formed between the first member 12 and second member 14 through the first plurality of barbs 16a and second plurality of barbs 16b when they are placed together.

Each of the barbs 16a of the first plurality of barbs 16a and each barbs 16b of the second plurality of barbs 16b extend from the first member 12 and second member 14, respectively, to a height no greater than 5 millimeters and preferably less than 0.5 millimeters. The first plurality of barbs 16a and second plurality of barbs 16b oppose each other. Preferably, the barbs 16a of the first plurality of barbs 16a and the barbs 16b of the second plurality of barbs 16b are of the same shape.

Figure 2:
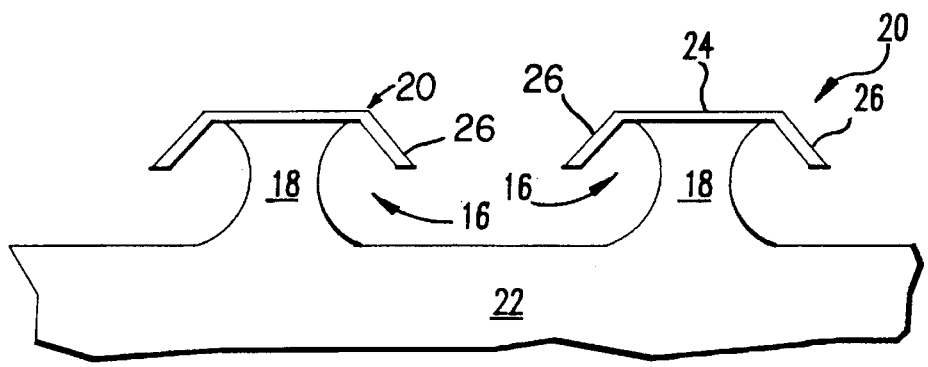
FIG. 2 is a schematic representation of a first plurality of barbs 16.
Figure 3:
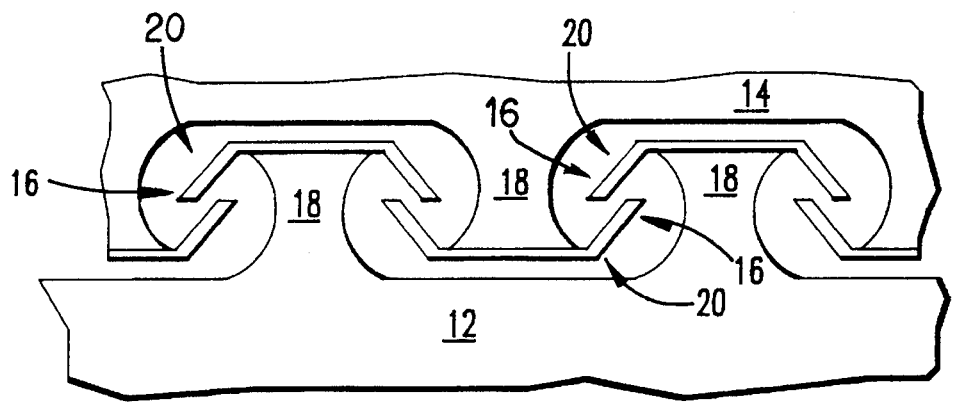
FIG. 3 is a schematic representation of a cross sectional view of a first plurality of barbs and second plurality of barbs in linking connection with each other.

As shown in FIG. 2, each barb 16 is comprised of a support 18 which extends from its respective member. Each barb is also comprised of a head 20 which is disposed upon the support 18 and which mates with the heads 20 of barbs 16 on the opposing plurality of barbs 16 as shown in FIG. 3.

In general, a micromechanical barb 16 can be used for linking with an object that will mate with the barb 16. A support 18 can extend from any type of a base 22, whether that base 22 be a first member 12 having other barbs 16a, or a second member 14 having barbs 16b, or whatever type of rigid material that is conducive to the formation and support of the barb 16. The rigid material is such that the barb which is made of it can sustain a locking relationship with other barbs or pierce an object and maintain a locking relationship therewith, as described below. Thus, essentially, a micromechanical barb 16 is comprised of a base 22. It is also comprised of a support 18 which extends from the base 22. Additionally, the barb is comprised of a head 20 which is disposed upon the support 18 and which mates with the object such that a locking connection is formed therebetween. The length of the support 18 and the head 20 are less than 5 millimeters. Preferably, the base 22, head 20 and support 18 are integral with each other.

The head 20 preferably has a central portion 24 which is connected to the support 18 and an extremity portion 26 which extends from the central portion 24 and which directly forms the locking connection with the object. The base 22, head 20 and support 18 are made of a rigid material. The rigid material can be, for instance, metal, ceramic, plastic, composite material or alloy. The metal could be steel, the ceramic could be aluminum oxide, the composite material could be graphite fiber matrix composite and the plastic polysulfone. Preferably, the base and support are made out of Si and the head is made out of $SiO_2$.

Figure 4:
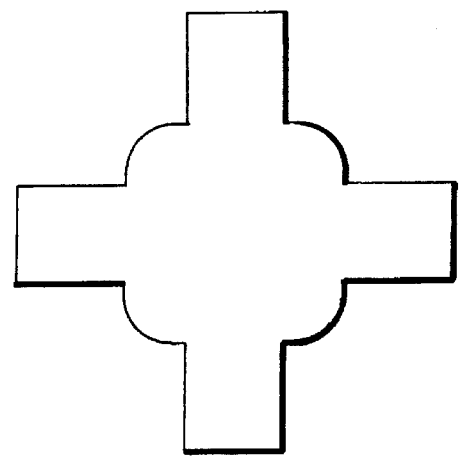
FIG. 4 is a schematic representation of an overhead view of a barb.
Figure 5:
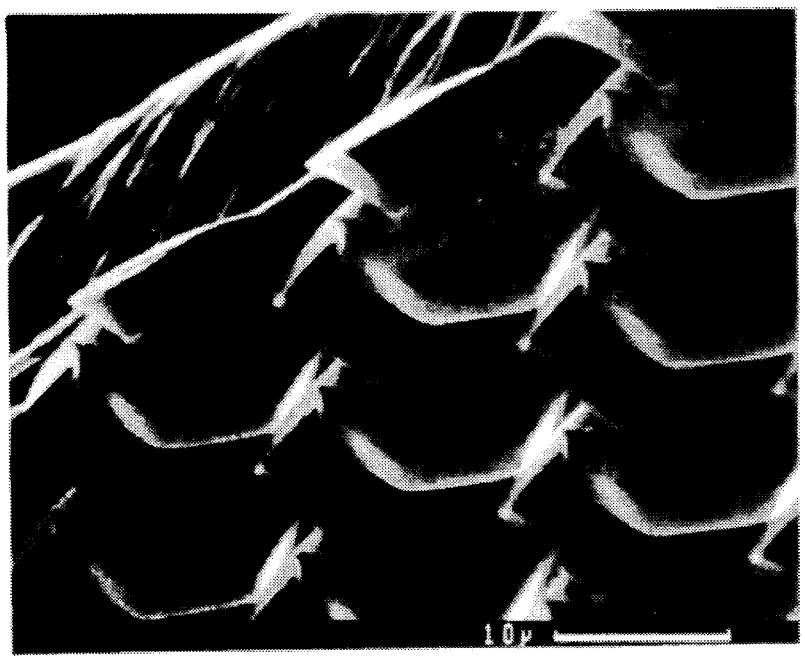
FIG. 5 is an electron micrograph of an array of barbs.

The extremity portion 26 preferably forms an angle θ, which is less than 90°, with the central portion 24 such that the extremity portion 26 extends from the central portion toward the base 22. The extremity portion 26 is preferably in the shape of a cross 28, as shown in FIG. 4 formed of four legs 30 to facilitate mating with another barb's 16 extremity portion 26 of identical shape. An electron micrograph of an array of mating micromechanical barb 16 is shown in FIG. 5. The central portion 24 of the head 20 in this picture is 1.0 μm $SiO_2$ on silicon support 18. Of course, the extremity portion can be of any shape that facilitates the latching of the object upon contact therewith by the head 22.

Figure 6:
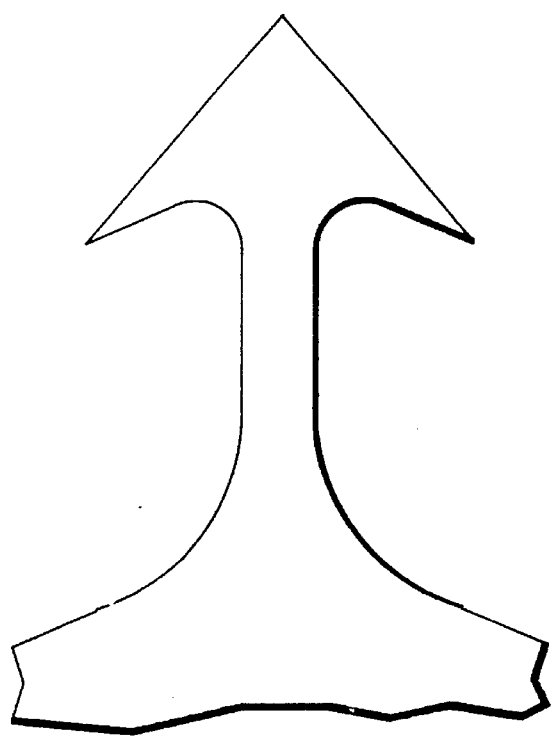
FIG. 6 is a side view of an alternative embodiment of a barb which pierces.
Figure 7:
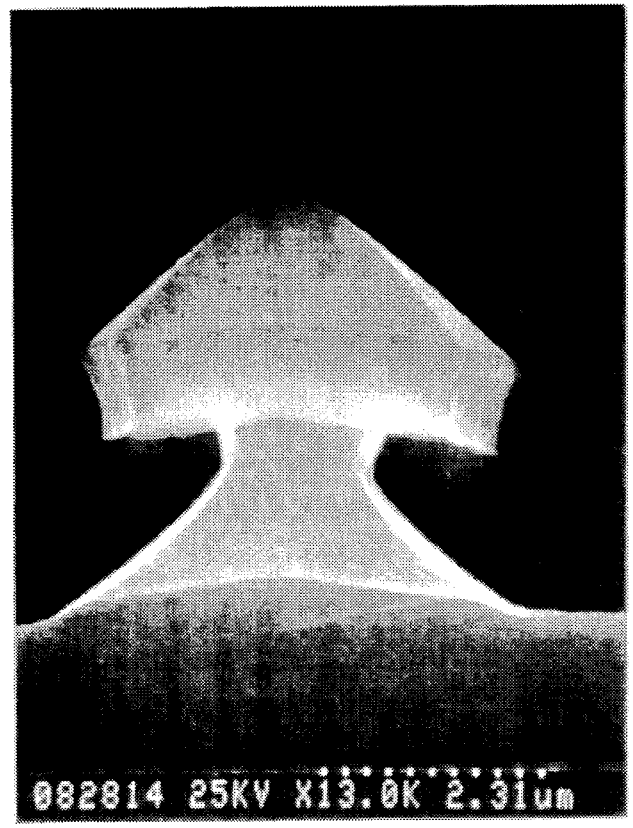
FIG. 7 is an electron micrograph of a piercing barb.

In an alternative embodiment the central portion 24 has a top surface 32 with a pointed shape that facilitates penetration of the first member 12 by piercing as shown in FIG. 6. FIG. 7 is an electron micrograph of a piercing micromechanical barb 16 that has a central portion 24 with a pointed shape that facilitates penetration of the first object.

Figure 14:
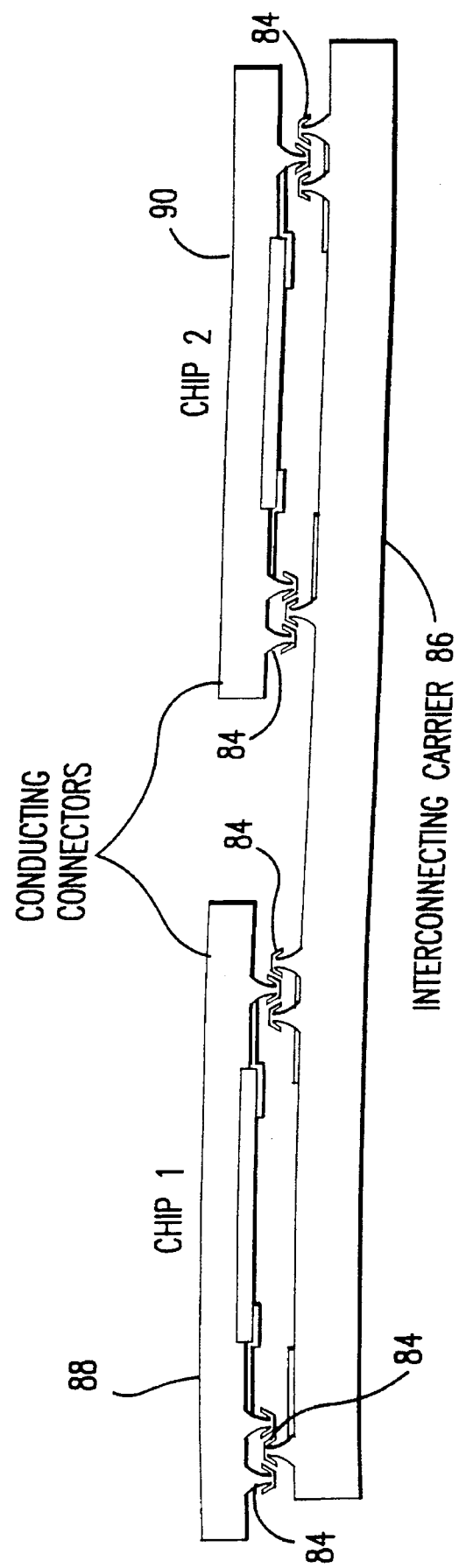
FIG. 14 is a schematic representation of electrical components being electrically connected when together with electrically conductive barbs.
Figure 15:
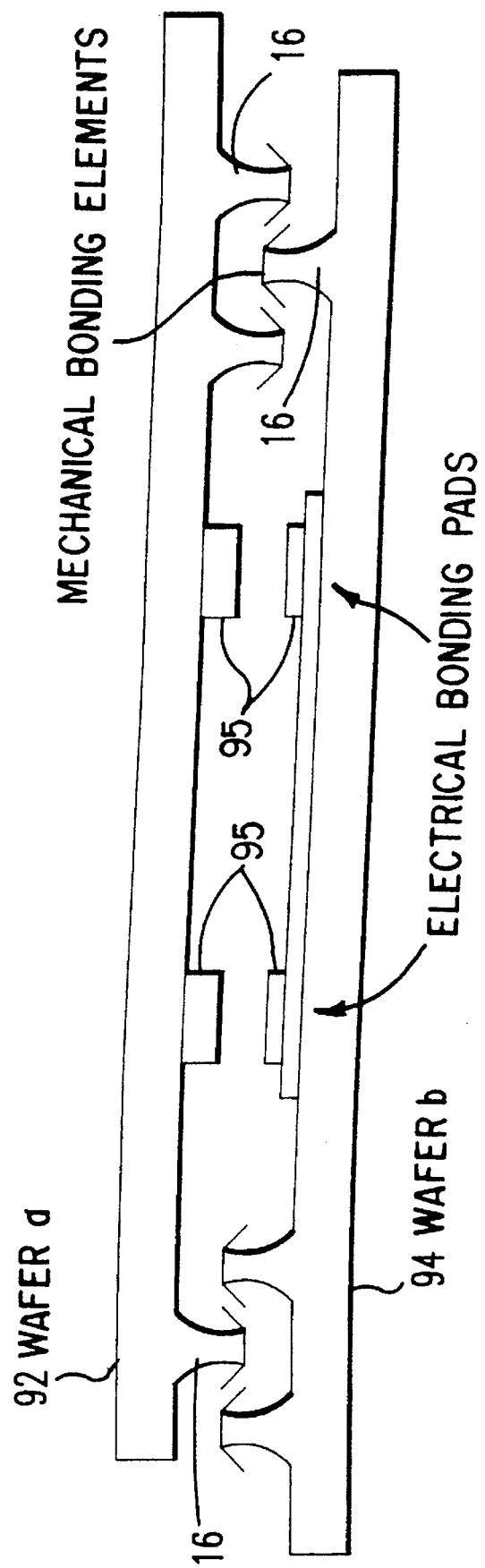
FIG. 15 is a schematic representation of electrical components being mechanically connected together with barbs.

The object can essentially be made of anything that is of a material that can be pierced by the central portion 24 with a pointed shape; or which can maintain a second array of barbs 16 that can mate with barbs extending from the base 22, and which is of a material that is also rigid enough to cause the extremity portion 26 to latch without separating if a predetermined level of force is not present. For example, the mating barbs 16 can be used as an electrical interconnect with respect to the input/output connections for an integrated circuit chip. The mating barbs 16 of the present invention provide a high quality electrical, thermal, and mechanical connection simultaneously, and can be fabricated directly on the chip with electronic circuitry. The inherently self-aligning aspect of the present invention (i.e., the mechanical compliance accommodates small misalignments) serve to facilitate the mounting of IC's on carriers, which is a major difficulty with present technology. As shown in FIG. 14, electrically conducting barbs 84 are electrically connected to an interconnecting carrier 86 and to a first IC 88 and a second IC 90. By connecting the first IC 88 and the second IC 90 to the interconnecting carrier 86 through the conducting barbs 84 electrical connector is formed therebetween. Alternatively, as shown in FIG. 15, a first semiconductor wafer 92 and a second semiconductor wafer 94 can be mechanically bonded together with barbs 16 while electrical bonding pads 94 on the wafers serve to electrically connect the wafers.

With respect to the piercing barb 16 that has a central portion 24 with a pointed shape it could be used to bond with objects having unprepared surfaces. For example, a surface consisting of piercing barbs 16 would be able to pierce skin or other tissues for medical applications. There could be an annulus studded on both sides with the piercing micromechanical barbs 16. As shown in FIG. 11, there is an apparatus 50 for connecting tissue. The apparatus 50, preferably an annulus 52, is comprised of a first side 54 and an opposing second side 56, as shown in FIG. 11b. On each side, there is a plurality of micromechanical barbs 58. These barbs 58 essentially piece the tissue 60 and hold it together. As is better shown in FIG. 11c, the tissue 60 can be a blood vessel 63 of some form, such as a vein or artery that is connected with the annulus 52. The opening 62 of the annulus allows the blood to flow therethrough. Preferably, the annulus 52 is comprised of segments 64 formed, for instance, by scored grooves in each side of the annulus 52. These grooves allow the annulus to have flexibility so it can bend, without breaking. This is important in circumstances where a pulse of force passes through the blood vessel 63, such as that associated with a heart beat. When the blood vessel 63 is attached under pressure to the annulus 52, the annulus breaks apart along the grooves.

Figure 12A:
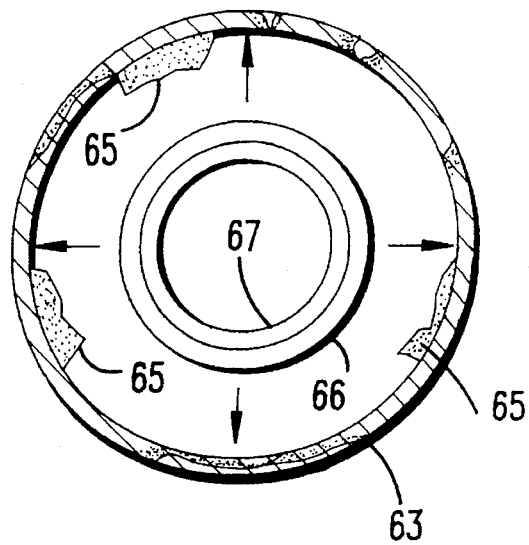
FIGS. 12a–c are schematic representations of an expandable cylinder for lining a blood vessel.
Figure 12B:
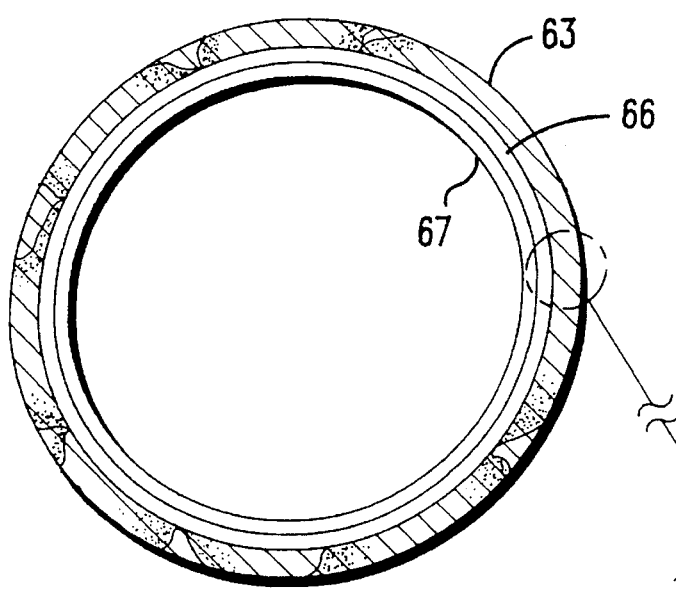
Figure 12C:
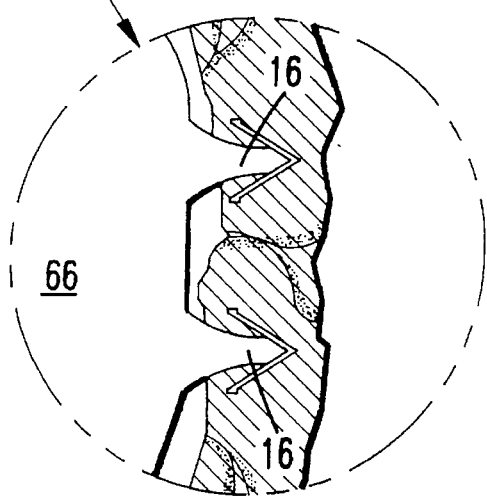

There could also be an expandable cylinder 66, the outside of which is blanketed with the piercing barbs 16, which undergo plastic deformation when expanded, a shown in FIG. 12. The expandable cylinder could be used as a stent for holding blood vessels open after angioplasty. For instance, plaque 65 in a blood vessel 63, as shown in FIG. 12a, can be removed by known techniques. Then, the expandable cylinder 66, with the barbs 16 about its outside surface, and which has a balloon 67 inside it, is inserted into the blood vessel 63. The balloon 67 is expanded, as shown in FIG. 12b, causing the cylinder 66 to expand and the barbs 16 on its outer surface to piece the blood vessel 63, resulting in the cylinder being held against the blood vessel 63 inner lining, as shown in FIG. 12c. The balloon 67 is then removed from the vessel 63 and the blood is allowed to flow unrestricted as before. However, with the cylinder 66 now in place, the vessel remains patent. The expandable cylinder 66 can be an elastomer not reactive with human fluids. Individual strips of the barbs 16 can be glued onto the surface of the cylinder 66.

Figure 13:
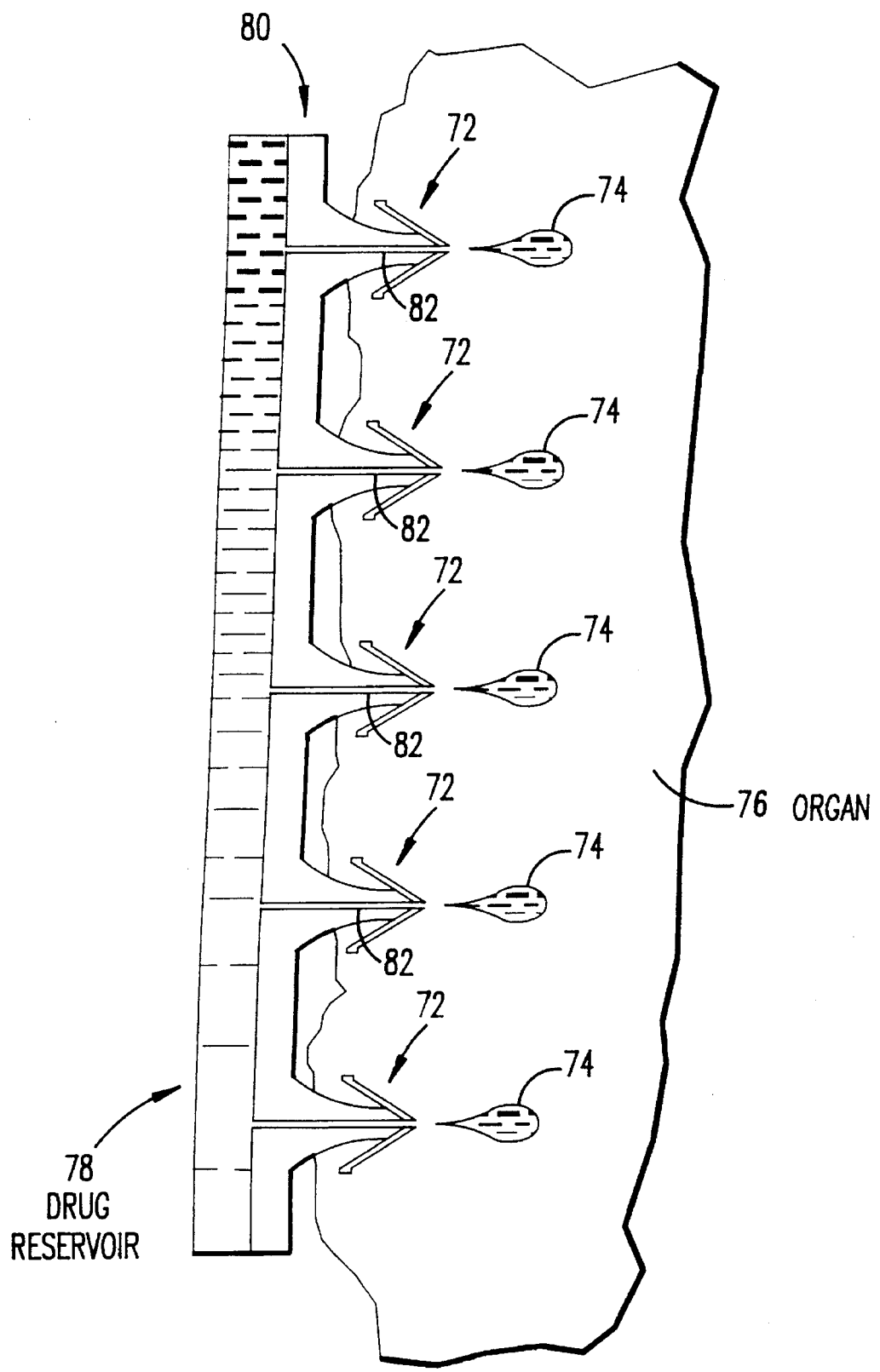
FIG. 13 is a schematic representation of an apparatus for providing a drug into an organ.

Hollow piercing barbs 72 could be used to deliver drugs 74 through them directly to the point of attachment on an organ 76, as shown in FIG. 13. A reservoir 78 in the base 80 holds the drug 76. A microminiature pump (not shown) could also be used to control the flow of the drug 76 into the organ. The hollow channel 82 in the barb 72 can be formed, for example, with a laser or an isotropic etch which penetrates into the base 80 only in one direction which does not spread out as it etches. The reservoir can be formed by etching the base so an opening is formed therein. The drug is then placed into the opening to form the reservoir. The base is then sealed by placing a cap over the opening.

Figure 8:
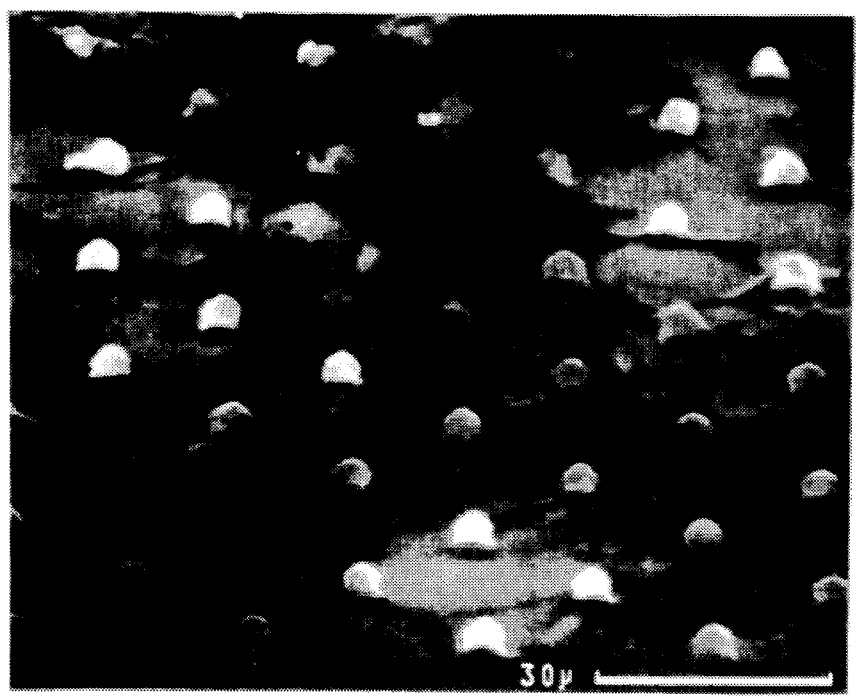
FIG. 8 is an electron micrograph of a plurality of piercing barbs in linking connection with the epithelial layer of a vena cava.

Additionally, sheets of piercing barbs 16 could be used as skin bandages to close incisions or wounds. FIG. 8 is an electron micrograph of a plurality of piercing barbs in linking connection with the epithelial layer of a vena cava. FIG. 8 reveals the barbs 16 penetrating the epithelial membrane of the vena cava.

Another use of the barbs 16 is in the interfacing of microdynamic machines to the macroscopic world. By their nature, submillimeter electromechanical devices, such as pressure, velocity and acceleration sensors, operate in a regime where mechanical contacts to the macroscopic "outside world" are problematical. The present invention provides an approach by which the vastly different scales of conventional and micromachining may be joined. The advantage of this method over fusion and electrostatic bonding include low temperature processing, absence of external chemical and electrical agents, and simplicity, e.g. wire bonding.

Figure 9A:
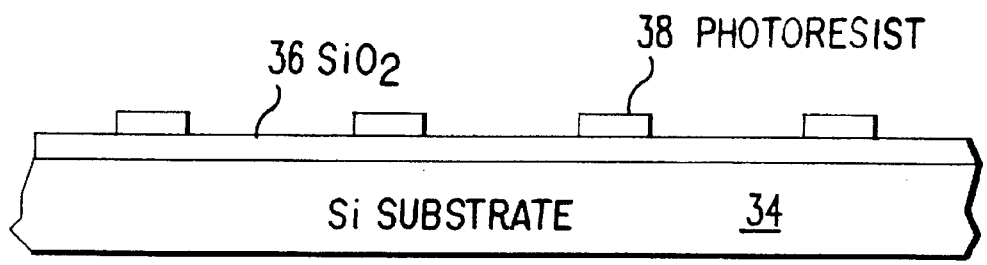
FIGS. 9a–d is a schematic representation of a process for producing barbs.
Figure 9B:
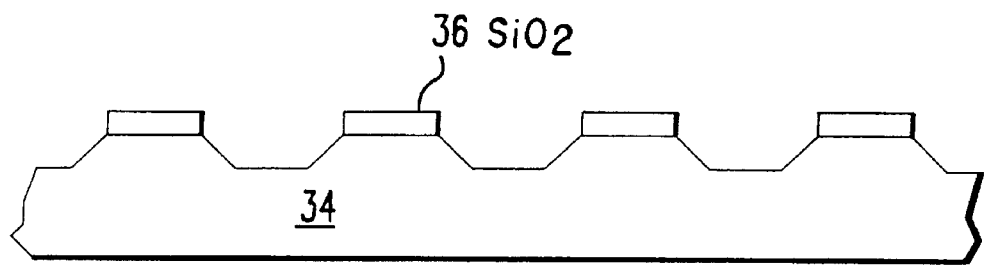
Figure 9C:
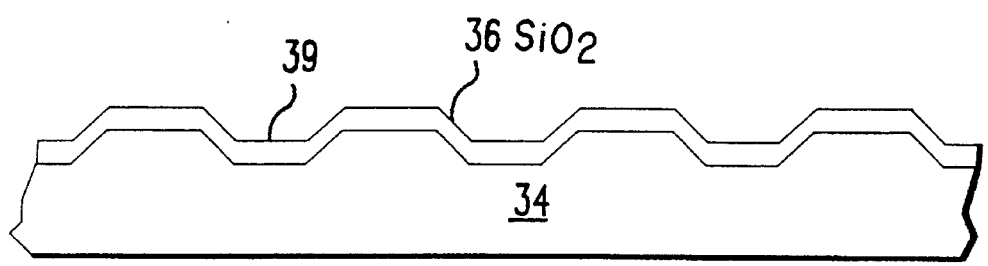
Figure 9D:
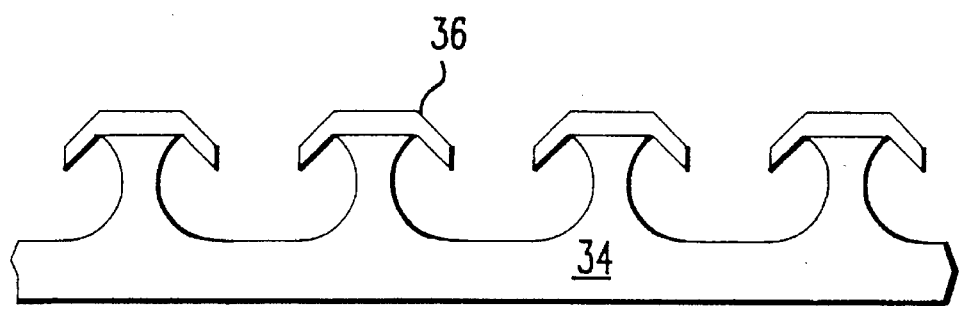

A method for making a plurality of barbs 16, and referring to FIGS. 9a–d, comprises the steps of first forming a substrate 34, such as Si or steel, with a layer 36 of a second material, such as $SiO_2$, thereon, and at predetermined discrete locations 28 on the layer 36 a third material, such as a photoresist as shown in FIG. 9a. Then, there is the step of removing portions of the layer 36 and the substrate 34 but not the third material such that a frustrum shape is formed on the surface of the substrate 34, as shown in FIG. 9b. Next, there is the step of removing the third material but leaving the first and second materials essentially untouched as shown in FIG. 9b. Then, there is the step of reforming the layer 36 made of the second material on the frustrum surface of the substrate 34 such that it also forms a frustrum shape, as shown in FIG. 9c. Next, there is the step of removing portions of the layer 36 at essentially the center of the lowest points of the frustrum of the layer 38. Then, there is the step of removing portions of the substrate 34 but not the layer 36 such that a plurality of barbs 16 is created as shown in FIG. 9d.

The various above embodiments essentially define a connector. The connector is comprised of a first portion which lockingly connects with an object, be it another connector or, for instance, tissue. The connector is also comprised of a base which the first portion is fixedly disposed. The first portion preferably includes a support which extends from the base; and a head which is disposed upon the support and which mates with the object such that a locking connection is formed therebetween, said length of the support and the head being less than 5 millimeters.

Preferably, the connector is produced by surface micromachining a full discussion of surface micromachining is found in "Silicon micromechanics: sensors and actuators on a chip" by R. Howe, R. Muller, K. Gabriel and W. Trimmer, IEEE Spectrum, pp. 29–35, Jul. 1990; and "Silicon Micromechanical Devices" by J. Angell, S. Terry and P. Barth, Scientific American, Vol. 248, No. 4, pp. 44–55, April 1983.

In the operation of the preferred embodiment, barbs 16 are formed having dimensions of approximately 4–18 μm wide× 4–18 μm long ×12 μm high. On a given base 22, there are approximately 200,000 individual barbs 16 per $cm^2$ of base 22. Two essentially identical but opposing plurality of barbs 16 are placed in contact. The application of a minimum compressive force corresponding to about 1.7 psi or 12 kPa to the bases 22 causes the barb 16 to deform and spring back, resulting in an interlocking of the first and second pluralities of barbs 16, (this compares to a value of $7 \times 10^5$ kPa (approximately $10^5$ psi) which is needed to crush either the first or second plurality of barbs 16.) Thus, the pluralities of barbs 16 self-align and mate. The mated structure has a tensile strength of approximately 1100 Pa, or about 160 psi. In essence, the mating of the first and second pluralities of barbs 16 act as a miniature, single-use, two-dimensional zipper.

Figure 10:
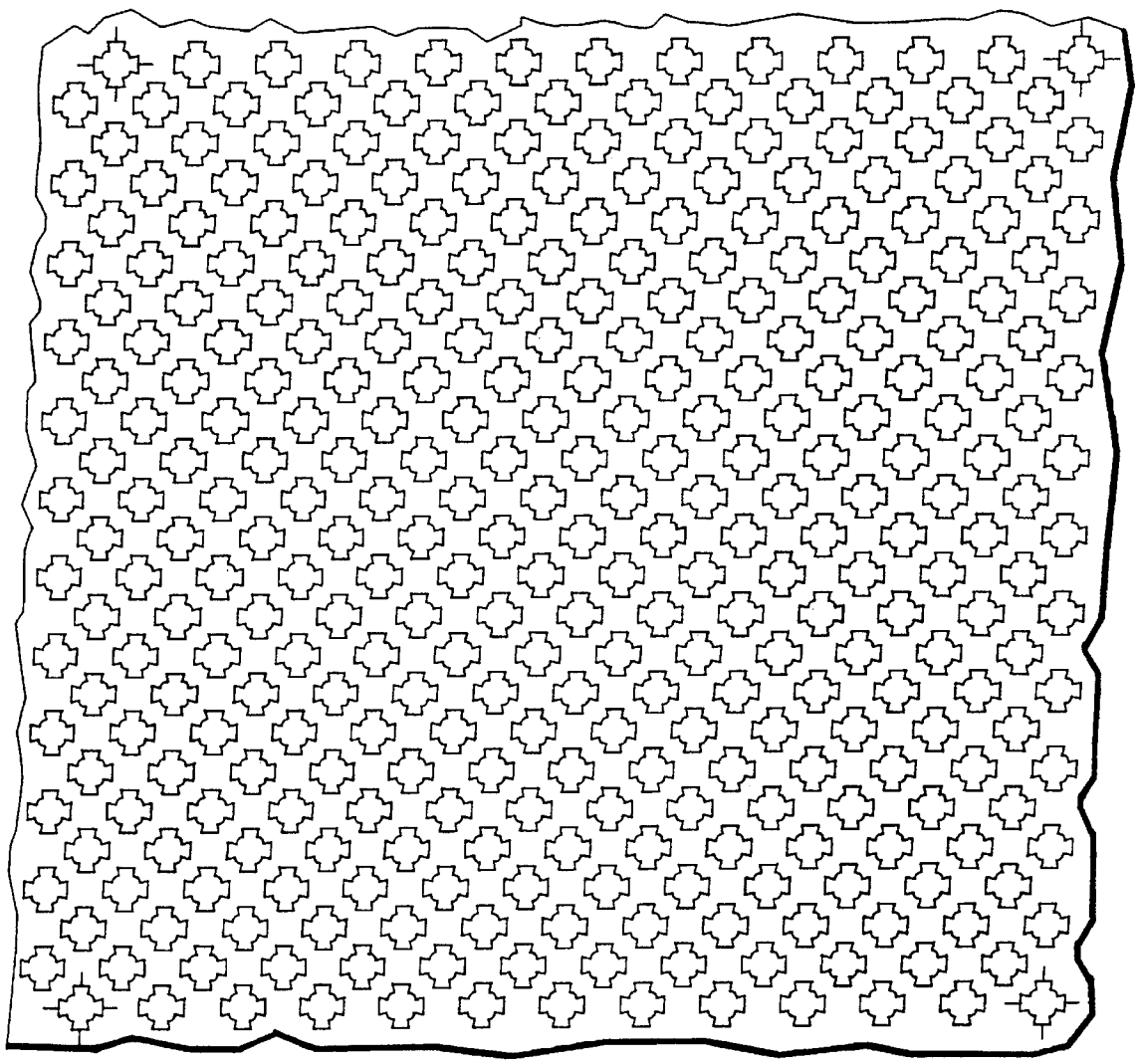
FIG. 10 is an overhead view of a mask pattern for use in the process depicted in FIG. 9.

FIG. 9 describes the process sequence. [100] oriented silicon wafers are thermally oxidized (1000 Å) and patterned into a matrix of 10 μm squares. The $SiO_2$ squares mask an anisotropic silicon etch in KOH, about 5 μm deep, to form a pattern of frustrums. The wafer is again oxidized, this time to a thickness of 1.0 μm, and patterned with the mask depicted in FIG. 10. The patterned oxide acts as a mask for the final step, an isotropic silicon etch to a depth of about 7 μm. An electron micrograph of the completed structure is shown in FIG. 6.

The second masking step in this process poses particular difficulties since the surface is highly nonplanar. The wafers are successfully patterned by using a nominal 2.1 μm thick photoresist film, coupled with a relatively long exposure time. The resist thickness, as measured from electron micrographs, is highly nonuniform; it reaches nearly 3.0 μm in the field regions, and is severely thinned over the tops of the frustrums. However, there is adequate thickness to prevent the $SiO_2$ caps from being attacked in the buffered HF etchant.

The isotropic silicon etch after the second masking step results in considerable lateral undercutting. To prevent this encroachment from weakening the Si support 18 supporting the $SiO_2$ head 20, two techniques are used: 1) the inside corners of the Greek cross mask pattern are filleted to reduce the undercutting; and 2) the isotropic etch (in $HNO_3$/ $CH_3COOH$/HF) is preceded by an anisotropic etch in KOH. This step reduces the undercutting by supplying most of the needed vertical clearance, without compromising the integrity of the Si support 18.

With respect to the piercing barb 16, this alternative embodiment can be fabricated also with a similar two mask process. The central portion 24 of the head 20 with a piercing barb 16 has a point with a radius of curvature $\geq 0.1$ μm.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed:

1. An apparatus for connecting to tissue, comprising: a member, the member having at least one surface upon which is disposed a plurality of micromechanical barbs, each of the plurality of micromechanical barbs having length no greater than 0.5 millimeters and being capable of piercing tissue and anchoring therein.

2. An apparatus as described in claim 1 wherein:

the member has a first surface for attaching to a first piece of tissue; and a second surface for attaching to a second piece of tissue, whereby the first piece of tissue can be connected to the second piece of tissue, each of the first surface and the second surface having a plurality of micromechanical barbs thereon, each of the plurality of micromechanical barbs having a length no greater than 0.5 millimeters and being capable of piercing tissue and anchoring therein.

3. An apparatus as described in claim 2 wherein the member is an annulus and wherein the tissue is a blood vessel, the annulus allowing blood from the blood vessel to flow therethrough.

4. An apparatus as described in claim 3 wherein the annulus is segmented with grooves to facilitate flexibility.

5. An apparatus for connecting to tissue, comprising: a member, the member having at least one surface upon which is disposed a plurality of micromechanical barbs, each of the plurality of micromechanical barbs being capable of piercing tissue and anchoring therein, each of the plurality of micromechanical barbs having:

a channel therethrough in fluid connection with a reservoir for holding a drug such that the drug is placed into fluidic communication with the tissue.

6. The apparatus of claim 5 wherein each of the plurality of micromechanical barbs has a length less than 0.5 millimeters.

7. An apparatus for connecting to tissue, comprising: a member, the member having a first surface and an opposing second surface, each of the first surface and the opposing second surface having a plurality of micromechanical barbs thereon, each of the plurality of micromechanical barbs being capable of piercing tissue and anchoring therein, each of the plurality of micromechanical barbs having a channel therethrough in fluid connection with a reservoir for containing a drug such that the drug is placed into fluidic communication with the tissue.

8. The apparatus of claim 7 wherein each of the plurality of micromechanical barbs has a length less than 0.5 millimeters.

9. The apparatus of claims 5, 7, or 1 wherein each of the plurality of micromechanical barbs comprises:

a. a support element attached to the member and extending from the member; and b. a head element disposed upon the support element, the head element including a top surface with a pointed shape to facilitate penetrating the tissue, the head element further including an extremity portion extending therefrom for anchoring the micromechanical barb in the tissue after piercing of the surface of the tissue, the support element and the head element having a combined length no greater than 0.5 millimeters.

10. The apparatus of claim 9 wherein the micromechanical barbs are fabricated from a material selected from the group consisting of a metal, a ceramic, a plastic and a composite material.

11. The apparatus of claim 9 wherein the micromechanical barbs are fabricated from $SiO_2$.

12. The apparatus of claim 9 wherein the extremity portion forms an angle of less that 90 degrees with the support element such that the extremity portion extends from the head element towards the member.

13. The apparatus of claim 9 wherein the extremity member comprises a cross-shaped member having four legs.

* * * * *